United States Patent [19]

Shug et al.

[11] Patent Number: 4,883,672
[45] Date of Patent: Nov. 28, 1989

[54] METHOD FOR PREVENTING DIET INDUCED CARNITINE DEFICIENCY IN DOMESTICATED DOGS AND CATS

[76] Inventors: Austin L. Shug, 1201 Shorewood Blvd.; Bruce W. Keene, 625 N. Blackhawk Ave., both of, Madison, Wis. 53705

[21] Appl. No.: 187,870
[22] Filed: Apr. 29, 1988
[51] Int. Cl.⁴ .............................................. A23K 1/00
[52] U.S. Cl. ....................................... 426/2; 426/635; 426/646; 426/805; 514/556
[58] Field of Search .................... 426/635, 2, 646, 805; 514/556

[56] References Cited

U.S. PATENT DOCUMENTS

| 4,254,147 | 3/1981 | Cavazza | 514/556 |
| 4,434,160 | 2/1984 | Jeretin et al. | 514/556 |
| 4,656,191 | 4/1987 | Fanelli | 514/556 |
| 4,689,226 | 8/1987 | Nurmi | 426/2 |
| 4,702,914 | 10/1987 | Ryan | 426/805 |

FOREIGN PATENT DOCUMENTS

| 0121441 | 9/1981 | Japan | 426/805 |
| 0126420 | 8/1982 | Japan | 514/556 |
| 2058566 | 4/1981 | United Kingdom | 514/556 |

OTHER PUBLICATIONS

Wolter, "Nutrition of Sport Animals", Lab. De Nutrition Sporture, Ecole Nationale Vet D'Alfort, vol. 2, 1987, pp. 63–94.

Primary Examiner—R. B. Penland
Attorney, Agent, or Firm—Carl E. Gulbrandsen

[57] ABSTRACT

A method is described for increasing the plasma L-Carnitine level in pets. A daily prophylactic amount of L-Carnitine is administered in the pet either as a dietary supplement in an amount of 0.2 to 2.0 grams of L-Carnitine per day, or L-Carnitine is provided as an additional ingredient to a commerical pet food in an amount of 0.2 to 2.0 grams of L-Carnitine per kilogram pet food.

7 Claims, No Drawings

METHOD FOR PREVENTING DIET INDUCED CARNITINE DEFICIENCY IN DOMESTICATED DOGS AND CATS

GENERAL FIELD OF THE INVENTION

The invention relates to the field of pet food compositions and more specifically to pet food enriched with L-Carnitine.

BACKGROUND OF THE INVENTION

L-Carnitine is a quaternary amine that promotes beta-oxidation of long-chain fatty acids by facilitating their transfer across the mitrochondrial membrane. L-Carnitine has also been shown to promote oxidation of branched-chain amino acids and the utilization of acetyl-coenzyme A.

In mammalian species, L-Carnitine concentration in cardiac and skeletal muscle is much higher than in serum. In these tissues fatty acids are utilized as a major source of energy. Because of L-Carnitine's central role in transporting fatty acids to the site of oxidation, adequate levels of a L-Carnitine are required for normal fatty acid and energy metabolism in mammalian hearts. This is evidenced by the restoration to normal of fatty acid oxidation in muscle homogenates of certain L-Carnitine deficient patients. A relationship between deficient levels of myocardial L-Carnitine and cardiomyopathy has been observed in both hamsters and dogs. Restoration toward normal of such deficient L-Carnitine levels has been shown to result in improved myocardial function in both species.

In mammals, L-Carnitine is derived from the diet and from biosynthesis in the liver, and in some species, kidney and other tissues. Neither cardiac nor skeletal muscle is capable of synthesizing L-Carnitine, however. Thus, the L-Carnitine found in these tissues was either absorbed from the diet or biosynthesized endogenously by other tissues.

The present invention is for a method of preventing diet-induced carnitine deficiency in domesticated dogs and cats using a dietary supplement containing a prophylactic amount of L-Carnitine. The invention is useful in preventing L-Carnitine deficiencies which can lead to a multitude of conditions, including myopathic heart disease, ischemic heart disease, hyperlipidemia, ketosis, muscle weakness and premature aging.

Pets, particularly the carnivores, are at great risk for developing L-Carnitine deficiencies. As Table 1 indicates, dog and cat foods are extremely low in free L-Carnitine levels as compared with that found in raw ground beef. Most pets are maintained strictly on commercial pet food diets and are thus kept chronically deficient in L-Carnitine. This results in a diet-induced carnitine deficiency.

TABLE 1

LEVEL OF FREE L-CARNITINE IN PET FOODS

| SAMPLE IDENTIFICATION | FREE L-CARNITINE "WATER SOLUBLE FRACTION" nanomoles/gram of product |
|---|---|
| GROUND BEEF | 3000.0 |
| ** SAMPLE TYPE: DRY DOG FOOD | |
| ALPO BEEF FLAVORED DINNER 5 LBS | 214.2 |
| CARNATION COME N GET IT 4 LBS | 53.6 |
| GAINES GRAVY TRAIN BEEF FLAVOR 5 LBS | 89.4 |
| KALKAN MEALTIME SMALL CRUNCHY BITS 5 LBS | 105.9 |
| KEN-L-RATION LOVE ME TENDER CHUNKS-BEEF | 27.3 |
| KEN-L-RATION KIBBLES 'N BITS 4 LBS | 78.6 |
| PETTS BRAND ALL NATURAL (HUBBARD) 4 LBS | 167.7 |
| PURINA DOG CHOW 5 LBS | 161.0 |
| PURINA CHUCKWAGON DOG CHOW | 72.7 |
| PURINA HI-PRO 5 LBS | 93.2 |
| PURINA BUTCHER'S BLEND BEEF, BACON, LIVER | 106.3 |
| PURINA FIT AND TRIM 4.5 LBS | 103.9 |
| PURINA PUPPY CHOW 5 LBS | 136.0 |
| NUTRO MAX PUPPY KIBBLE PUPPY FOOD | 143.5 |
| NUTRO MAX KIBBLE DOG FOOD | 192.7 |
| IAMS MINI CHUNKS | 182.9 |
| EUKANUBA (BY IAMS) | 216.3 |
| ** SAMPLE TYPE: SEMI-MOIST DOG FOOD | |
| GAINES BURGERS - BEEF 36 OZ | 55.5 |
| KEN-L-RATION SPECIAL CUTS 24 OZ | 59.2 |
| ** SAMPLE TYPE: CANNED DOG FOOD | |
| ALPO BEEF & LIVER DINNER 14 OZ | 222.8 |
| ALPO LAMB CHUNKS | 89.2 |
| CARNATION MIGHTY DOG BEEF 6.5 OZ | 1799.1 |
| CARNATION MIGHTY DOG TURKEY & GIBLETS | 172.3 |
| GAINES CYCLE 2 (ADULT) BEEF 14 OZ | 28.6 |
| GAINES CYCLE 1 (PUPPY) 14 OZ | 208.9 |
| KALKAN CHOPPED MEATY COMBO 14 OZ | 129.7 |
| KEN-L-RATION CHICKEN, BEEF, LIVER DINNER | 33.9 |
| KEN-L-RATION CHICKEN DINNER | 30.2 |
| RECIPE HEARTY MEAT DINNER 14 OZ | 95.5 |
| VETS-BEEF FLAVORED 15 OZ | 62.5 |
| ** SAMPLE TYPE: DRY CAT FOOD | |
| KALKAN CRAVE 18 OZ | 135.7 |
| CARNATION FRISKIES OCEAN FISH FLAVOR | 168.6 |
| STARKIST 9 LIVES CRUNCHY MEALS REAL TUNA & EGG | 114.0 |
| IAMS CAT FOOD 26 OZ | 196.9 |
| PURINA CAT CHOW 22 OZ | 109.1 |
| PURINA KITTEN CHOW 18 OZ | 121.4 |
| PURINA MEOW MIX 18 OZ | 61.2 |

TABLE 1-continued
LEVEL OF FREE L-CARNITINE IN PET FOODS

| SAMPLE IDENTIFICATION | FREE L-CARNITINE "WATER SOLUBLE FRACTION" nanomoles/gram of product |
| --- | --- |
| PURINA TENDER VITTLES MOIST CHICKEN DINNER | 127.8 |
| PURINA THRIVE 18 OZ | 95.2 |
| PURINA SPECIAL DINNERS SEA NIP DINNER 18 OZ | 188.2 |
| **  SAMPLE TYPE: CANNED CAT FOOD** | |
| STARKIST AMORE TURKEY & GIBLET DINNER 3 OZ | 94.0 |
| STARKIST AMORE POACHED SALMON DINNER 3 OZ | 101.2 |
| CARNATION FRISKIES BUFFET TURKEY & GIBLET 6 OZ | 80.0 |
| CARNATION FRISKIES BUFFET SEAFOOD SUPPER 6 OZ | 180.5 |
| CARNATION FANCY FEAST BEEF & LIVER GOURMET 3 OZ | 364.6 |
| CARNATION FANCY FEAST FANCY SEAFOOD FEAST 3 OZ | 115.4 |
| KALKAN TENDER TURKEY DINNER 6 OZ | 142.0 |
| STARKIST 9 LIVES LIVER & CHICKEN DINNER 6 OZ | 64.5 |
| STARKIST 9 LIVES OCEAN WHITEFISH DINNER 6 OZ | 134.3 |
| PURINA 100 TUNA 6 OZ | 294.3 |
| PURINA BEEF & LIVER DINNER 6 OZ | 595.6 |

EXAMPLE 1

Six apparently healthy Greyhound dogs were determined to be normal by physical examination, fecal flotation, complete blood count, serum biochemical profile, ECG, and echocardiography. They were fed a standard commercial dog food diet free choice for a one-month control period. Control plasma samples (as well as subsequent test samples) were obtained following an eight-hour fast on two consecutive days for analysis of total, free, and esterified L-Carnitine concentration. The average of the plasma L-Carnitine concentration on two consecutive days was taken for each dog and each measuring period.

Following the control period, all of the dogs were continued for two weeks on the standard commercial dog food diet supplemented with L-Carnitine. The L-Carnitine supplement was in the form of 0.5 kg per dog per day of raw frozen lean ground beef. This was equivalent to a daily supplement of 350 mg. of L-Carnitine per dog. Plasma samples were drawn on days 7 and 8 (averaged for the one-week measurement) and days 13 and 14 (averaged for the two-week measurement) for L-Carnitine analysis. Differences between the means of each test period and control were determined by the Student's t test.

Results

The results of the study are shown in Table 2.

TABLE 2

| Dog # | PLASMA CARNITINE CONCENTRATIONS, U MOLES/LITER. | | | | | | | | |
| --- | --- | --- | --- | --- | --- | --- | --- | --- | --- |
| | Control | | | Week 1 | | | Week 2 | | |
| | Total | Free | Ester | Total | Free | Ester | Total | Free | Ester |
| 1 | 29.6 | 25.0 | 4.5 | 70.1 | 58.9 | 11.2 | 52.4 | 44.9 | 8.0 |
| 2 | 38.7 | 32.2 | 6.5 | 70.7 | 60.5 | 10.2 | 65.7 | 62.2 | 3.5 |
| 3 | 27.2 | 26.1 | 1.2 | 57.2 | 52.5 | 4.7 | 58.1 | 52.7 | 2.2 |
| 4 | 31.9 | 30.5 | 1.4 | 63.1 | 55.6 | 3.4 | 56.3 | 52.0 | 4.3 |
| 5 | 23.1 | 20.0 | 3.1 | 58.1 | 56.0 | 2.1 | 66.3 | 58.5 | 8.7 |
| 6 | 27.6 | 23.4 | 4.2 | 56.3 | 51.7 | 4.8 | 43.2 | 41.0 | 2.2 |
| AVG | 31.8 ± | 26.2 ± | 3.4 ± | 62.5* ± | 55.9** ± | 6.0 ± | 57.0 ± | 51.9* | 4.8 ± |
| S.D. | 5.0 | 4.5 | 2.0 | 6.5 | 3.5 | 3.7 | 8.6 | 8.0 | 2.8 |

Control is after 1 month of commercial dog food only. Week 1 and 2 are after 1 and 2 weeks of ground beef supplementation (0.5 kg/day/dog) respectively.
*Denotes statistical significance at $p \leq 0.05$
**Denotes statistical significance at $p \leq 0.01$ The data in Table 2 indicates that the plasma L-Carnitine concentration of a normal, healthy dog, previously maintained on a commercial pet food diet, is significantly increased if such pet food is supplemented with adequate levels of L-Carnitine.

It is clearly evident from the foregoing data that supplementation with a prophylactic amount of L-Carnitine of the standard commercial dog food will dramatically increase the plasma concentration of L-Carnitine in dogs.

It is to be understood that although the foregoing Example details the use of raw frozen lean ground beef as an L-Carnitine source, other sources within the scope of the claims can be readily utilized in the application of the invention with essentially equivalent results. For example, meat or meat by-products may be used other than raw frozen lean ground beef. These meat or meat by-products may be heat processed, dried or frozen and are suitable substitutes provided such meat or meat by-products have an L-Carnitine concentration in the range of 0.2 to 2.0 grams L-Carnitine per kilogram. The term "meat" is understood to apply not only to the flesh of cattle, but also that of other mammals, poultry and fish. The term "meat by-products" is intended to refer to those non-rendered parts of the carcass of slaughtered animals including but not restricted to mammals, poultry and the like.

Also within the scope of the claims would be the use of commercially prepared L-Carnitine such as that obtained from Austin Chemical Company, Inc., 9655 West Bryn Mawr Avenue, Rosemont, Ill.

These L-Carnitine supplements may be administered separately in the form of dietary supplements or they may be added at the time of manufacture of the commercial dog food as an additional ingredient in the commercial dog food. If used as a separate dietary supplement, the L-Carnitine may be combined with other valuable nutritional or prophylactic substances. Examples of this would be a combination of L-Carnitine with a vitamin and mineral preparation. Another example would be the inclusion of a prophylactic amount of L-Carnitine with an anti-heartworm medication such as diethylcarbamazine.

The L-Carnitine supplement may also be administered as a liquid preparation. L-Carnitine is extremely soluble in water. Such a liquid preparation may be prepared by dissolving the appropriate amount of L-Carnitine in a waterbased solution. Flavoring agents or other nutritional or prophylactic substances may likewise be combined in the solution. The liquid preparation may be administered to the pet separately as a dietary supplement. It may be added to the pet's drinking water or to the animal's food. Further, the concentration of L-Carnitine in the liquid preparation may be such that the appropriate amounts in the range of 0.2 to 2.0 grams of L-Carnitine may be easily measured out and administered as above described to the animal daily.

Having thus described the invention, what is claimed is:

1. A method for preventing diet-induced carnitine deficiency in a domesticated dog or cat, comprising the step of: administering daily to said dog or cat a prophylactic amount of L-Carnitine.

2. A method as described in claim 1, wherein said L-Carnitine is administered by adding said L-Carnitine to said dog or cat's pet food so as to form a mixture and feeding said mixture to said dog or cat.

3. A method as claimed in claim 2, wherein said mixture has an L-Carnitine concentration of at least 700 mg. L-Carnitine per kilogram mixture.

4. A method as described in claim 1, wherein said L-Carnitine is administered by dissolving said prophylactic amount of L-Carnitine in said dog or cat's drinking water so as to form a solution and feeding said solution to said dog or cat.

5. A method as claimed in claim 4, wherein said solution has an L-Carnitine concentration of at least 700 mg. L-Carnitine per liter of solution.

6. A method as claimed in claim 1, wherein said prophylactic amount is an amount sufficient to produce and maintain in said dog or cat plasma total carnitine concentration of at least 40.0 $\mu$M/liter of plasma.

7. A method for preventing diet-induced carnitine deficiency in a domesticated dog or cat comprising the steps of: mixing a sufficient amount of L-Carnitine with said dog or cat's food so as to form a mixture having an L-Carnitine concentration of at least 700 mg. per kilogram of mixture; feeding daily said mixture to said dog or cat.

* * * * *

REEXAMINATION CERTIFICATE (1566th)

United States Patent [19]

Shug et al.

[11] B1 4,883,672
[45] Certificate Issued  Oct. 8, 1991

[54] METHOD FOR PREVENTING DIET INDUCED CARNITINE DEFICIENCY IN DOMESTICATED DOGS AND CATS

[76] Inventors: Austin L. Shug, 1201 Shorewood Blvd.; Bruce W. Keene, 625 N. Blackhawk Ave., both of Madison, Wis. 53705

Reexamination Request:
No. 90/002,067, Jun. 25, 1990

Reexamination Certificate for:
Patent No.: 4,883,672
Issued: Nov. 28, 1989
Appl. No.: 187,870
Filed: Apr. 29, 1988

[51] Int. Cl.$^5$ .............................................. A23K 1/00
[52] U.S. Cl. ..................................... 426/2; 426/635; 426/646; 426/805; 514/556
[58] Field of Search ................... 426/2, 635, 646, 805; 514/556

[56] References Cited

FOREIGN PATENT DOCUMENTS 0126420 8/1982 Japan.

OTHER PUBLICATIONS

Greyhound Breeding, Raising and Training, as Viewed by 25 Prominent Breeders and Trainers, reprinted from The Greyhound Review, (Apr., Jun., Jul., Sep., Dec. 1979; Apr., May, Jun., Aug., Oct., 1980) pp. 34, 41–44, 53 and 64–69. Copies available from: The National Greyhound Association, P.O. Box 543, Abilene, Kansas 67410.
C. J., Rebouche, PhD, "Carnitine Metabolism and Deficiency Syndromes", Mayo Clin. Proc., Aug. 1983, vol. 58, pp. 533–540.
A. Etzioni et al., "Systemic Carnitine Deficiency Exacerbated by a Strict Vegetarian Diet", Archives of Disease in Childhood, vol. 59, No. 2, Feb. 1984, pp. 177–179.
Orzali et al., "Carnitine re Lipid Metabolism," Part II, The Journal of Pediatrics, Mar. 1984, pp. 436–440.
T. Kamikawa, "Effects of L-Carnitine on Exercise Tolerance in Patients with Stable Angina Pectoris," Jpn. Heart J., Jul. 1984, pp. 587–597.
Casciani et al., "Effect of L-Carnitine on Lipid Pattern in Haemodialysis", The Lancet, Dec. 13, 1980, pp. 1309–1310.
Yoshikazu Suzuki, M.D., Masayasu Narita, M.D., and Noboru Yamazaki, M.D., "Effects of L-Carnitine on Arrhythmias during Hemodialysis", vol. 23, No. 3, May 1982, Jpn. Heart J., pp. 349–359.
M. E. Tripp and A. L. Shug, "Plasma Carnitine Concentrations in Cardiomyopathy Patients", Biochemical Medicine 32, 1984, pp. 199–206.
M. E. Tripp, et al., "Systematic Carnitine Deficiency Presenting as Familial Endocardial Fibroelastosis", The New England Journal of Medicine, Aug. 13, 1981, vol. 305, No. 7, pp. 385–390.
Cederbaum, M.D. et al., "Four-Year Treatment of Systemic Carnitine Deficiency", Correspondence, vol. 310, No. 21, New Engl. J. Med., May 24, 1984, pp. 1395–1396.
M. Novak et al., "The Effect of a L-Carnitine Supplemented Soybean Formula on the Plasma Lipids of Infants", Clinical Conference on Pediatric Nutrition, Acta Chirurgica Scandinavica, Supplementum 517, pp. 149–155.
P. R. Chapoy, M.D. et al., "Systemic Carnitine Deficiency A Treatable Inherited Lipid-Storage Disease Presenting as Reyes Syndrome", The New England Journal of Medicine, Dec. 11, 1980, pp. 1389–1394.
D. Rudman, et al., "Carnitine Deficiency in Cirrhosis", Carnitine, Biosynthesis, Metabolism, and Functions, Academic Press, 1980, pp. 308–317.
C. J. Rebouche, et al., "Carnitine Metabolism and Function in Humans," Ann. Rev. Nutr. 1986, pp. 41–66.
P. R. Borum, "Regulation of the Carnitine Concentration in Plasma in Rats", Carnitine Biosynthesis Metabolism, and Functions, Academic Press, 1980, pp. 115, 119.
G. M. Vacha, et al., "L-Carnitine on Hypertriglyceridemia". The American Journal of Clinical Nutrition 38: Oct. 1983, pp. 532–540.
L. J. Waber, et al., "Carnitine Deficiency Presenting as Cardiomyopathy", The Journal of Pediatrics, Nov., 1982, pp. 700–705.
A. C. Engel, MD and C. J. Rebouche, PhD, "Pathogenetic Mechanisms in Human Carnitine Deficiency Syndromes", Disorders of the Motor Unit, 1982, pp. 643–656.
Curran, J. S., et al., "An Evaluation of Orally Supplemented L-Carnitine in Premature Infants Receiving Intralipid ®20%", Clinical Conference on Pediatric Nurition, Acta Chirurgica Scandinavica, Supplementum, pp. 157–164.
Di Donato, S., et al., "Systemic Carnitine Deficiency. Clinical, Biochemical, and Morphological Cure with L-Carnitine", Neurology 34, Feb. 1984, pp. 157–162.

*Primary Examiner*—R. B. Penland

[57] ABSTRACT

A method is described for increasing the plasma L-Carnitine level in pets. A daily prophylactic amount of L-Carnitine is administered in the pet either as a dietary supplement in an amount of 0.2 to 2.0 grams of L-Carnitine per day, or L-Carnitine is provided as an additional ingredient to a commercial pet food in an amount of 0.2 to 2.0 grams of L-Carnitine per kilogram pet food.

REEXAMINATION CERTIFICATE ISSUED UNDER 35 U.S.C. 307

THE PATENT IS HEREBY AMENDED AS INDICATED BELOW.

Matter enclosed in heavy brackets [] appeared in the patent, but as been deleted and is no longer a part of the patent; matter printed in italics indicates additions made to the patent.

AS A RESULT OF REEXAMINATION, IT HAS BEEN DETERMINED THAT:

Claims 1, 4 and 7 are determined to be patentable as amended.

Claims 2, 3, 5 and 6 dependent on an amended claim, are determined to be patentable.

1. A method for preventing diet-induced carnitine deficiency in a domesticated dog or cat [,] *fed a daily diet of water and pet food, said pet food being substantially free of raw, red meat, the method* comprising the step of: administering daily to said dog or cat a prophylactic amount of *substantially pure* L-carnitine.

4. A method as described in claim 1, wherein said L-Carnitine is administered by dissolving said prophylactic amount of *substantially pure* L-Carnitine in said dog or cat's [drinking] water so as to form a solution and feeding said solution to said dog or cat.

7. A method for preventing diet-induced carnitine deficiency in a domesticated dog or cat *fed a daily diet of water and pet food, said pet food being substantially free of raw, red meat, the method* comprising the steps of: mixing a sufficient amount of *substantially pure* L-Carnitine with said dog or cat's *pet* food so as to form a mixture having an L-Carnitine concentration of at least 700 mg. per kilogram of mixture; feeding daily said mixture to said dog or cat.

* * * * *